US011950780B2

(12) United States Patent
Li et al.

(10) Patent No.: US 11,950,780 B2
(45) Date of Patent: Apr. 9, 2024

(54) SURGICAL INSTRUMENT AND BATTERY PACK THEREOF

(71) Applicant: REACH SURGICAL, INC., Tianjin (CN)

(72) Inventors: Yu Li, Tianjin (CN); Kai Wang, Tianjin (CN); Rongxuan Feng, Tianjin (CN)

(73) Assignee: REACH SURGICAL, INC., Tianjin (CN)

( * ) Notice: Subject to any disclaimer, the term of this patent is extended or adjusted under 35 U.S.C. 154(b) by 45 days.

(21) Appl. No.: 17/655,819

(22) Filed: Mar. 22, 2022

(65) Prior Publication Data
US 2022/0211373 A1 Jul. 7, 2022

Related U.S. Application Data

(63) Continuation of application No. PCT/CN2020/115563, filed on Sep. 16, 2020.

(51) Int. Cl.
*A61B 17/00* (2006.01)
*A61B 17/072* (2006.01)
*H01M 10/44* (2006.01)

(52) U.S. Cl.
CPC ....... *A61B 17/07207* (2013.01); *H01M 10/44* (2013.01); *A61B 2017/00398* (2013.01);
(Continued)

(58) Field of Classification Search
CPC ........ A61B 17/068; A61B 2017/00734; A61B 17/00; A61B 17/072; H01M 10/441
See application file for complete search history.

(56) References Cited

U.S. PATENT DOCUMENTS 5,207,697 A * 5/1993 Carusillo ........... A61B 17/1628
  408/124
9,314,261 B2 * 4/2016 Bales, Jr. ............... A61B 50/20
(Continued)

FOREIGN PATENT DOCUMENTS

CN 102048567 A 5/2011
CN 103096818 A 5/2013
(Continued)

OTHER PUBLICATIONS

Extended European Search Report, dated Oct. 5, 2022, from European App. No. 20953500.4, 8 pages.
(Continued)

*Primary Examiner* — Gloria R Weeks
(74) *Attorney, Agent, or Firm* — Workman Nydegger

(57) ABSTRACT

A surgical instrument and a battery pack for use with the surgical instrument are disclosed. The surgical instrument includes a handle assembly, having a protruding portion; and a battery pack, detachably assembled on the handle assembly, operated by the protruding portion, and having a battery unit, where the battery pack includes a discharging system comprising a discharge element, and a switching member, operated to electrically connect the discharge element to the battery unit of the battery pack to form a discharge circuit, and having an initial open state, in which the discharge circuit is non-conductive, an intermediate open state, in which the switching member cooperates with the protruding portion to make the discharge circuit non-conductive, and a closed state, in which the switching member is separated from the protruding portion to make the discharge circuit conducting.

18 Claims, 11 Drawing Sheets

(52) U.S. Cl.
CPC .............. *A61B 2017/0046* (2013.01); *A61B 2017/00734* (2013.01); *A61B 2560/0214* (2013.01)

(56) References Cited

U.S. PATENT DOCUMENTS

| | | | | |
|---|---|---|---|---|
| 2006/0091858 | A1* | 5/2006 | Johnson | H02J 7/0034 320/128 |
| 2006/0164032 | A1* | 7/2006 | Johnson | H02J 7/04 320/103 |
| 2009/0071675 | A1* | 3/2009 | Hanawa | H02J 7/0031 173/217 |
| 2009/0143805 | A1* | 6/2009 | Palmer | A61N 7/02 606/169 |
| 2012/0071711 | A1 | 3/2012 | Shelton et al. | |
| 2012/0071796 | A1* | 3/2012 | Smith | A61B 17/320092 601/3 |
| 2016/0249919 | A1* | 9/2016 | Savage | H01M 10/613 227/175.1 |
| 2017/0202608 | A1* | 7/2017 | Shelton, IV | H01M 6/14 |
| 2018/0198294 | A1* | 7/2018 | Sheeks | H01M 10/6554 |
| 2020/0127339 | A1 | 4/2020 | Nakano et al. | |
| 2020/0297343 | A1* | 9/2020 | Satti, III | A61B 17/1155 |
| 2022/0387040 | A1* | 12/2022 | Liu | H02J 7/0063 |
| 2023/0138097 | A1* | 5/2023 | Forsell | A61F 5/004 606/139 |

FOREIGN PATENT DOCUMENTS

| | | |
|---|---|---|
| CN | 104956561 A | 9/2015 |
| CN | 206026379 U | 3/2017 |
| CN | 107809968 A | 3/2018 |
| CN | 208130022 U | 11/2018 |
| CN | 110137731 A | 8/2019 |
| EP | 0351179 A1 | 1/1990 |
| EP | 2510891 | 10/2012 |
| EP | 3151308 A1 | 4/2017 |

OTHER PUBLICATIONS

Chinese First Office Action, dated Jun. 16, 2022, from Chinese App. No. 202080002034.8, 29 pages.

* cited by examiner

SURGICAL INSTRUMENT AND BATTERY PACK THEREOF

CROSS-REFERENCE OF RELATED APPLICATIONS

The application is a continuation application of International Application No. PCT/CN2020/115563 filed on Sep. 16, 2020, which is hereby incorporated by reference in its entirety.

TECHNICAL FIELD

The present disclosure relates to the technical field of medical instrument, and in particular to a battery-powered surgical device and the battery pack thereof.

BACKGROUND

More and more surgical instruments are powered by the battery pack comprising at least one battery unit. Such instruments comprise a variety of electric tools and may be used in various surgical environments. Surgical instruments may comprise staplers, cutters, graspers, suturing devices, RF cutters/coagulators, ultrasonic cutters/coagulators, laser cutters/coagulators, and other instruments that require battery power. For example, a stapler is a medical device that may be used in place of suturing manually, and is a surgical instrument that may be used to cut off and anastomose tissues by using titanium staples. With the advancement of electric stapler technology and the widespread promotion of its clinical application, the advantages of the electric stapler technology in clinical surgery have been recognized by more and more doctors. Compared with the traditional manual stapler, the electric stapler needs to be used with a power supply device, for example, a common lithium battery may be used for power supply.

Due to the structural principle characteristics of the lithium battery, the power dissipation of the lithium battery occurs during a storage process, and the electric stapler is required to have a certain storage validity period. Therefore, when the lithium battery is designed, the amount of the electric power in the lithium battery often exceeds the electric power required in actual use of the electric stapler. Therefore, after the use of the electric stapler, the amount of the power left in the lithium battery is usually still sufficient. If the lithium battery is improperly treated, it may cause explosion or fire and other hazards. Therefore, how to safely and harmless treat the lithium battery after use becomes an urgent problem to be solved, which affects a large-scale application of the electric staplers.

In the prior art, when the lithium battery is mounted in the battery compartment of the electric stapler, a protruding portion in the battery compartment will be connected to the discharge circuit in the battery device, thus the power in the lithium battery is consumed in a relatively small current through the discharge circuit, while outputting a large current through the electronic control circuit of the electric stapler to supply the DC motor to achieve a desired forward and reverse operation. After the lithium battery is taken out from the battery compartment, the lithium battery continues to be discharged through the discharge circuit, and the amount of the power of the lithium battery may be reduced to a safe threshold range within a predetermined time. However, in the prior art, the lithium battery of the electric stapler is discharged while working, and the working voltage of the motor usually has a lower limit and an upper limit, and when the electric stapler is fired at thick tissues, the lithium battery needs to provide an very high working current instantaneously, and the lithium battery is limited by an inherent design output power, which inevitably leads to the instantaneous and rapid decrease of the potential difference between the positive electrode and negative electrode at the output terminals of the lithium battery. When the potential difference between the positive electrode and negative electrode at the output terminal of the lithium battery is reduced to less than the lower limit of the motor's working voltage, the motor stops running, and the electric stapler is not able to complete the desired cutting and suturing function.

SUMMARY

Therefore, the technical problem to be solved by the present disclosure is how to overcome the defect in the prior art, in which the potential difference between the positive electrode and negative electrode of the battery output terminals is prone to be lower than the lower limit of the working voltage of the motor when powering the motor, which makes it difficult for the motor to operate normally. Therefore, the present disclosure is to provide a battery pack in which the potential difference between the positive electrode and negative electrode of the battery output terminals is less likely reduced to be less than the lower limit of the working voltage of the motor when powering the motor, and a surgical instrument powered by the battery pack.

In order to solve the above technical problem, according to one aspect of the present disclosure, the present disclosure provides a surgical instrument, comprising: a handle assembly, having a protruding portion; and a battery pack, detachably assembled on the handle assembly, and operatively coupled to the protruding portion, and having at least one battery unit; wherein, the battery pack comprises at least one discharging system comprising: a discharge element, and a switching member, operable to electrically connect the discharge element to the battery unit of the battery pack to form a discharge circuit; wherein, the switching member has an initial open state, in which the discharge circuit is non-conductive; an intermediate open state, in which the switching member cooperates with the protruding portion to make the discharge circuit non-conductive, and a closed state, in which the switching member is released from the protruding portion to make the discharge circuit conducting.

Furthermore, the battery pack further comprises a mounting body that comprises a housing, and a frame; wherein, the battery unit is assembled on the frame, and the housing covers the frame, and the frame further comprises a recess adapted for receiving the protruding portion.

Furthermore, a battery dock is provided on the handle assembly for receiving the battery pack, and the protruding portion is arranged therein.

Furthermore, the discharging system further comprises a discharging circuit board, on which the discharge element is arranged, and the switching member is configured to be at least one conductive movable member with at least part operably movable, and one end of the movable member is fixed on the discharging circuit board and electrically connected to the discharge element, and the other end thereof is operably connected to the discharge element electrically.

Furthermore, at least part of the movable member is an elastic member.

Furthermore, when the switching member is in the intermediate open state, the protruding portion forces the movable member at a position where the movable member is in non-conductive connection with the discharge element.

Furthermore, an aperture is arranged on the discharge circuit board, adapted for receiving at least a portion of the switching member.

Furthermore, the movable member comprises a fixed portion, a movable portion, operably to be electrically connected to the discharge element, and a transition portion, arranged between the fixed portion and the movable portion.

Furthermore, when the switching member is in the initial open state, the movable portion of the movable member abuts against a side wall of the aperture of the discharge circuit board, and is non-conductively connected to the discharge element.

Furthermore, the discharging circuit board is arranged on a side wall of the recess of the frame of the battery pack.

Furthermore, the switching member comprises a blocking member and a conductive member, and the blocking member and/or the conductive member are/is operable to switch the switching member between the initial open state, the intermediate open state and the closed state.

Furthermore, the blocking member is adapted for causing the switching member to be in the initial open state, and is operated by the protruding portion to be disabled from blocking the switch member, so as to cause the switching member to be in the intermediate open state.

Furthermore, the switching member is arranged on a proximal side of the recess of the frame of the battery pack, and is electrically connected to the discharge element.

Furthermore, the conductive member comprises separable conductive elastic pieces, wherein when the switching member is in the initial open state, the blocking member is arranged between free ends of the conductive elastic pieces to isolate the conductive elastic pieces from each other.

Furthermore, the switching member comprises a blocking member, and a conductive member having a separable conductive elastic piece, wherein when the switching member is in the initial open state, the blocking member is arranged between free ends of the conductive elastic pieces to isolate the conductive elastic pieces from each other.

Furthermore, the blocking member is actuated by the protruding portion to be released from the conductive member.

Furthermore, when the switching member is in the intermediate open state, the protruding portion is respectively in contact with the free ends of the conductive elastic pieces, so as to isolate the conductive elastic pieces from each other.

Furthermore, when the free ends of the conductive elastic members are engaged with each other, the switching member is switched to the closed state, and the discharge circuit is conducting.

Furthermore, the switching member comprises a first switch and a second switch, and the first switch and/or the second switch are/is operable to be electrically connected with the discharge element, so as to switch the switching member between the initial open state, the intermediate open state and the closed state.

Furthermore, the blocking member is configured as a first switch, and the conductive member is configured as a second switch.

Furthermore, the first switch is operable to control the second switch.

Furthermore, the first switch is configured as a self-locking switch.

Furthermore, the second switch is an electronic switch.

Furthermore, the second switch is a photoelectric switch.

Furthermore, a fin portion is arranged on the protruding portion and is operable to control the first switch and/or the second switch.

Furthermore, when the switching member is in the initial open state, the first switch is switched off and the second switch is not conductive.

Furthermore, when the switching member is in the intermediate open state, the first switch is turned on through the fin portion of the protruding portion, and the second switch is remained to be closed through the fin portion.

Furthermore, when the switching member is in the closed state, the first switch and the second switch are both conductive, allowing the discharge circuit to be conductive.

Furthermore, the switching member comprises a normal-close switch, the state of which is depended on a stop member, wherein the stop member is operated to switch the switching member between the initial open state, the intermediate open state, and the closed state.

Furthermore, the blocking member is configured as a stop member, and the conductive member is configured as a normal-close switch.

Furthermore, the stop member is a stop plate.

Furthermore, a tip is arranged on the protruding portion, and operably to disable the stop member from blocking, so as to switch the switching member to the intermediate open state.

Furthermore, when the switching member is in the initial open state, the stop member abuts against the normal-close switch to switch off the normal-close switch.

Furthermore, when the switching member is in the intermediate open state, the protruding portion disables blocking function of the stop member, and the protruding portion abuts against the normal-close switch to keep the normal-close switch off.

Furthermore, when the switching member is in the closed state, the protruding portion is released from the normal-close switch to switch it to the closed state, allowing the discharge circuit to be conductive.

According to another aspect of the present disclosure, it provides a battery pack comprising at least one battery unit, further comprising at least one discharging system having: a discharging element, and a switching member, operably to be in electrical connection with the discharging element to the battery unit of the battery pack to form a discharge circuit; the switching member has an initial open state, in which the discharge circuit is non-conductive, an intermediate open state, in which the switching member is operated to cause the discharge circuit to be non-conductive, and a closed state, in which the switching member is operated to allow the discharge circuit to be conductive.

Furthermore, the battery pack comprises a mounting body, provided with a housing, and a frame, wherein, the battery unit is assembled on the frame and the housing covers the frame, and the frame further comprises a recess suitable for receiving the protruding portion.

Furthermore, the discharging system further comprises a discharging circuit board provided with the discharging element, and the switching member is configured to be at least one conductive movable member, and at least portion of the movable member is operated to move, and one end of the movable member is fixed on the discharging circuit board and electrically connected to the discharge element, and the other end of the movable member is operated to be electrically connected to the discharge element.

Furthermore, the switching member comprises a blocking member and a conductive member, and the blocking member and/or the conductive member are/is operable to switch the switching member between the initial open state, the intermediate open state and the closed state.

Furthermore, the blocking member is adapted for making the switching member to be in the initial open state, and is operably to be functionally disabled from blocking so as to switch the switching member to the intermediate open state.

Furthermore, the switching member is arranged on a proximal side of the frame of the battery pack, and is electrically connected to the discharge element.

Furthermore, the conductive member comprises separable conductive elastic pieces, and when the switching member is in the initial open state, the blocking member is arranged between free ends of the conductive elastic pieces to isolate the conductive elastic pieces from each other.

Furthermore, the switching member comprises a blocking member, and a conductive member that comprises a separable conductive elastic piece, and when the switching member is in the initial open state, the blocking member is arranged between free ends of the conductive elastic pieces to isolate the conductive elastic pieces from each other.

Furthermore, the switching member comprises a first switch and a second switch, and the first switch and/or the second switch are/is operably to be electrically connected with the discharging elements, so as to switch the switching member between the initial open state, the intermediate open state, and the closed state.

Furthermore, the blocking member is configured as a first switch, and the conductive member is configured as a second switch.

Furthermore, the switching member comprises a normal-close switch and a stop member, the state of which is depended on the stop member, wherein the stop member is operated to switch the switching member between the initial open state, the intermediate open state, and the closed state.

Furthermore, the blocking member is configured as a stop member, and the conductive member is configured as a normal-close switch.

BRIEF DESCRIPTION OF THE DRAWINGS

In order to more clearly describe the technical solutions in the specific embodiments of the present invention or in the prior art, the drawings used in the description of the specific embodiments or the prior art will be briefly introduced hereinafter. Apparently, the appended drawings described below represents some embodiments of the present invention, and other drawings may be obtained on the basis of these drawings by a person skilled in the art without making creative efforts.

DETAILED DESCRIPTION

Figure 1:
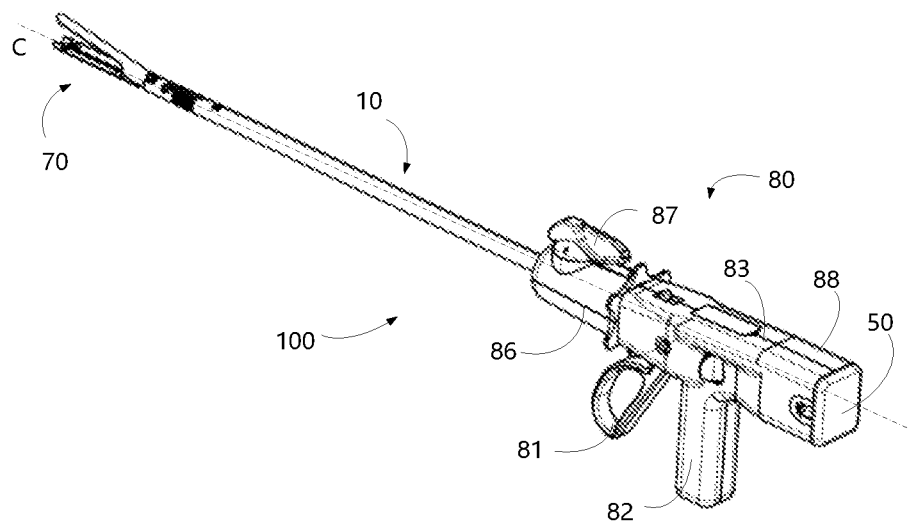
FIG. 1 is a schematic structural view of an electric surgical instrument provided by an embodiment of the application.

The technical solutions in the embodiments of the present invention will be described clearly and completely with reference to the drawings. Apparently, the described embodiments only represent part of but not all of the embodiments of the present invention. Based on the embodiments of the present invention, all other embodiments obtained by a person skilled in the art without making creative efforts fall within the scope of the present invention.

In addition, the technical features involved in the different embodiments of the present disclosure described below may be combined with each other as long as they do not conflict with each other.

In the various embodiments of the present disclosure, the terms "distal end/distal side/distal portion" refers to the end/side/portion of the surgical instrument away from an operator during operation, and the terms "proximal end/proximal side/proximal portion" refers to the end/side/portion of the surgical instrument close to the operator during operation.

A number of embodiments of the present disclosure relate to battery-powered surgical instruments and battery packs that comprise structures that is beneficial for shipping, storage, and treatment. For example, in an embodiment of the present disclosure, the battery pack may comprise at least one battery located in a housing which defines a cavity. The battery pack may have a discharging system arranged in the cavity, the discharging system includes a switching member and a discharge element, and the switching member may switched among a first state, a second state, and a third state. The surgical instrument used in combination with the battery pack may comprise a protruding portion, a battery dock, or other battery pack receiving/connecting portion. The protruding portion may be arranged on a base assembly of the instrument, and may also be arranged on a grip portion of the instrument handle assembly. Before getting connected to the surgical instrument, the switching member is in a first state, such as an initial open state. When the battery pack is connected to the surgical instrument, the protruding portion may be used to operate the switching member to reach a second state, such as an intermediate open state. The switching member is operated by the protruding portion to change its position so as to be in a second state, such as an intermediate open state. The protruding portion is removed from the switching member to reach a third state, such as a closed state. When the switching member is in a closed state, the anode, the cathode and the discharge element of the battery unit are electrically connected to form a discharge circuit. In some embodiments, the discharge element is a resistance element. After the battery pack is removed from the surgical instrument, the power is consumed through the discharge circuit from the battery units. In some embodiments, the battery pack also comprises a plurality of such discharging systems.

Before describing the embodiments of the battery unit, the battery, the battery pack and related surgical instrument, embodiments of the surgical instruments powered by batteries are firstly described in details in the present disclosure. Although the surgical instrument described herein comprise electrosurgical instruments for cutting and suturing, it should be understood that the battery units and battery packs described herein may be used in combination with any suitable type of electrosurgical instruments, such as cutters, holders, suturing devices, RF cutter/coagulators, ultrasonic cutters/coagulators, laser cutters/coagulators, etc.

FIG. 1 is a schematic structural view of an example of a surgical instrument 100. The embodiment as shown is an endoscopic instrument. In general, the example of the surgical instrument 100 described herein is an endoscopic surgical cutting and stapling instrument. However, it should be indicated that according to other embodiments, the surgical instrument may also be a non-endoscopic surgical cutting and stapling instrument, such as an open surgical instrument for open surgery.

Specifically, the surgical instrument 100 shown in FIG. 1 comprises a handle assembly 80, an elongated body 10, and an end effector 70, wherein the elongated body 10 extends distally from the handle assembly 80, and the end effector 70 is assembled on a distal portion of the elongated body 10, in which the end effector 70 is adapted to perform specific surgical operations, such as clamping, suturing/stapling, cutting, etc. on tissues. As further shown in FIG. 1, the handle assembly 80 comprises a trigger 81 and a grip portion 82. When the trigger 81 is pulled towards the gripping portion 82, jaws of the end effector 70 may be closed. In addition, the trigger 81 may also be configured to control the output of a power supplier of the surgical instrument 100.

It should be noted that although one of the embodiments of the surgical instrument 100 described herein is configured with an end effector 70 for cutting anastomosing tissue, in alternative embodiments, other technologies for cutting or anastomosing tissue may also be used. For example, end effectors that applies RF energy or adhesives to anastomose tissues may also be used.

As further shown in FIG. 1, the surgical instrument 100 according to one of the embodiments of the present disclosure further comprises a rotating knob 86 assembled on the distal portion of the handle assembly 80 and fixed with the proximal portion of the elongated body 10. When the rotating knob 86 is operated to rotate about a longitudinal axis C of the surgical instrument 100, the elongated body 10 and the end effector 70 are rotated accordingly. In addition, the surgical instrument 100 according to the one of embodiments of the present disclosure further comprises a articulation knob 87, which is rotatably mounted on the rotating knob 86, adapted e for articulating the end effector 70 when being operated.

Figure 2:
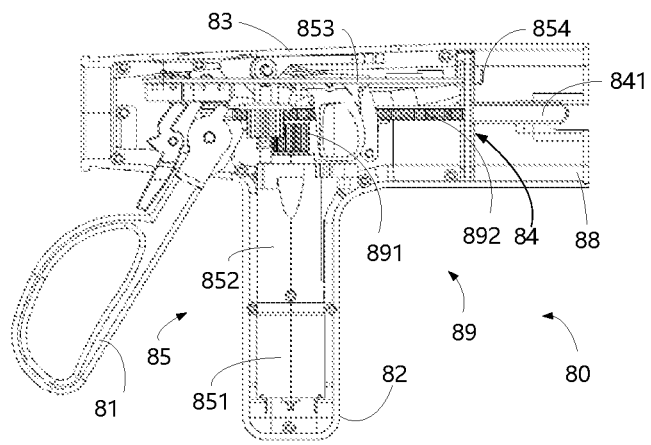
FIG. 2 is a schematic structural view the electric surgical instrument handle assembly in FIG. 1.

With further reference to FIG. 2, it shows an internal structure of the handle assembly 80 of the surgical instrument 100 provided by one of the embodiments. The power supplier 85 is arranged in a housing 83, providing power for the surgical instrument 100. A control device 853 is also disposed inside housing 83 to control the output of the power supplier 85 to output power, and the control device 853 may be a control circuit board. The power supplier 85 used for the surgical instrument 100 may be a motor of any form, as long as it may meet the specific output form and requirements of the surgical instrument 100. For example, the power supplier 85 of the surgical instrument 100 in this embodiment adopts a DC brush motor, and the functions of electric firing (forward) and electric retreat of the surgical instrument 100 may be achieved through the forward and reverse rotation of the motor. Certainly, the power supplier 85 may also adopt other types of motors such as a DC brushless motor.

The handle assembly 80 also comprises an actuation mechanism 89 that comprises a gear assembly 891, a rack assembly 892, and a drive rod. The gear assembly 891 is connected to an output of the power supplier 85 and the rack assembly 892 respectively, and a distal portion of the drive rod is arranged in the elongated body 10, and a proximal portion of the drive rod is coupled with the rack assembly 892. In other embodiments, the power supplier 85 is further provided with a gear box 852, and the motor 851 is coupled to the gear assembly 891 through the gear box 852 so as to provide power for the surgical instrument 100.

Figure 3:
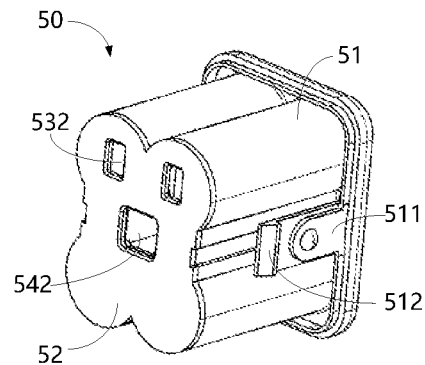
FIG. 3 is a schematic structural view of the battery pack in FIG. 1.
Figure 4:
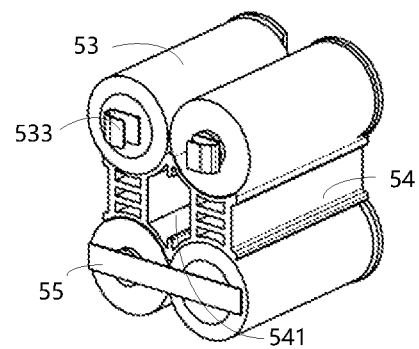
FIG. 4 is a schematic structural view of an interior of the battery pack in FIG. 3.
Figure 5:
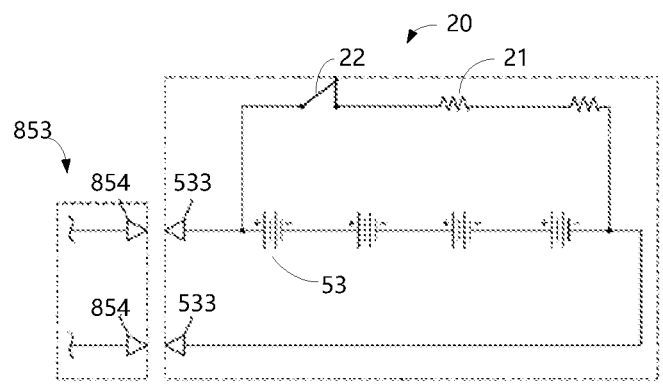
FIG. 5 is a working principle view of an electrical circuit of the electric surgical instrument communicating with the discharge circuit.

As shown in FIG. 1 and FIG. 2, the handle assembly 80 of the surgical instrument 100 according to the embodiment may allow at least one battery pack 50 to be received therein. In one of the embodiments, a battery dock 88 for receiving the battery pack 50 is arranged on the handle assembly 80. The battery pack 50 is detachably assembled in the battery dock 88. The battery pack 50 may include a single battery or a plurality of batteries arranged in a series and/or parallel configuration. FIG. 3 and FIG. 4 show the specific structure of the battery pack 50, comprising at least one battery unit 53 and a mounting body adapted for receiving the battery unit 53. As shown in FIG. 3 and FIG. 4, the mounting body comprises a housing 51, a frame 54 and a cover 52; the housing 51 is sleeved on an outside of the frame 54, and the battery unit 53 is assembled on the frame 54. A plurality of battery units 53 may be arranged in series and/or in parallel configuration. For example, when there are two or more battery units 53, the battery units 53 are connected by conductors 55, such that the plurality of battery units 53 are connected in series. In this embodiment, there are four battery units 53 connected in series. Two battery units 53 at two ends of the series are respectively provided with output terminals 533. Correspondingly, the cover 52 is provided with an aperture 532 allowing the output terminal 533 to pass through. A conductive terminal 854 disposed on the control device 853 is operatively in electrical connection to the output terminal 533 of the battery pack 50, as shown in FIG. 2 and FIG. 5, so as to provide power to the surgical instrument 100.

In addition, a base assembly 84 is fixed or detachably arranged in the battery dock 88. When the battery pack 50 is assembled and received within the battery dock 88, at least part of the base assembly 84 is coupled to the battery pack 50. In other embodiments, a variety of other structures may be used to achieve functions of the base assembly 84. For example, in one example, the base assembly 84 comprises a protruding portion 841 that is operably received by the battery pack 50. For example, a recess 541 is arranged in the frame 54 of the mounting body of the battery pack 50, which is adapted for receiving the protruding portion 841 of the base assembly 84. Preferably, the protruding portion 841 is arranged perpendicular to the base assembly 84 and is located in a center of the battery base to facilitate insertion into the recess 541 of the frame 54 of the battery pack 50.

In addition, as shown in FIG. 3, the housing 51 of the battery pack 50 is also provided with a mounting member 511, and a fixing protrusion 512 is arranged on the mounting member 511. The battery pack 50 is detachably mounted in the battery dock 88 of the handle assembly 80 through the mounting member 511, the fixing protrusion 512 is adapted for fixing a relative position of the battery pack 50 and the battery dock 88.

Figure 6:
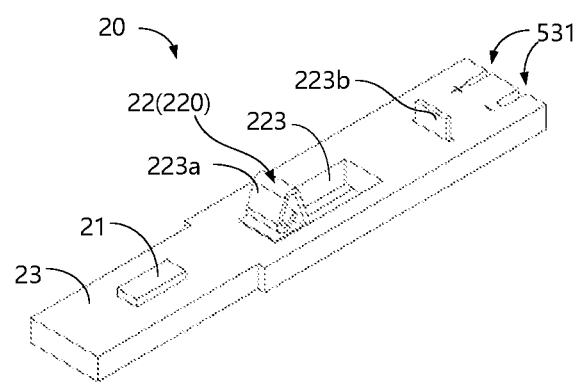
FIG. 6 is a schematic structural view of a circuit board of an embodiment of the application.
Figure 19:
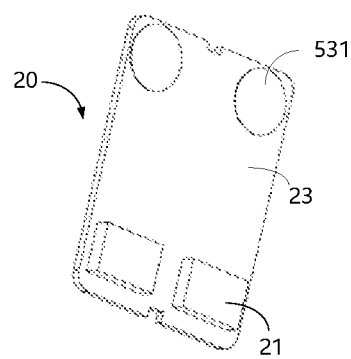
FIG. 19 is a schematic structural view of a discharging circuit board according to another embodiment of the application.

Furthermore, the battery pack 50 of one of the embodiments of the present disclosure further comprises a discharging system 20, adapted for conducting discharging of the battery pack 50, releasing the power of the battery units 53 of the battery pack 50 down to a safe threshold. The discharging system 20 comprises a switching member 22 and a discharge element 21 disposed on the discharging circuit board 23. The discharge element 21 may be a resistance element, and the resistance element may be any suitable resistance element having any suitable resistance and/or impedance. A terminal 531 is further disposed on the discharging circuit board 23 (for example, as shown in FIG. 6 and FIG. 19), which is adapted to be electrically connected to the terminal 533 of the battery unit 53, so as to operatively connect the discharging system 20 and the battery unit 53 electrically. The switching member 22 has an initial open state, an intermediate open state, and a closed state. For example, when the switching member 22 is in the initial open state or the intermediate open state, the discharging element 21 is not electrically connected to the battery unit 53; when the switching member 22 is in the closed state, the discharging element 21 is electrically connected to the battery unit 53 of the battery pack 50. FIG. 5 shows part of the circuit principle of the battery unit 53, the discharging system 20 and the control device 853 in the battery pack 50.

When the battery pack 50 is in the initial unused state, the switching member 22 is positioned in the initial open state, and the discharge circuit is not conductive, forming the first state of the discharging system 20; and after the battery pack 50 is assembled in the handle assembly 80 of the surgical instrument 100, the switching member 22 is still operated in the open state, that is to say, the intermediate open state, and the discharge circuit is non-conductive, forming a second state of the discharging system 20; after the battery pack 50 is used, being detached from the surgical instrument 100, the switching member 22 is operated to switch to the turn-on state, and the discharge circuit is conducted, forming a third state of the discharging system 20. When the battery pack 50 has been fully discharged, it may be treated as non-hazardous waste. The structure of the discharging system 20 will be described in detail with reference to specific embodiments hereafter.

Embodiment 1

FIGS. 6 to 12 show a specific example of a battery pack 50 and a discharging system 20 thereof provided by the present disclosure, where the discharging system 20 comprises a switching member 22, one end of which is fixed to the discharging circuit board 23, being electrically connected to the discharge element 21. The switching member 22 has an initial open state, an intermediate open state that may be operated, and a closed state, which correspond to the first state, the second state, and the third state of the discharging system 20, respectively. The discharging system 20 of one of the embodiments will be described with reference to specific structures.

Figure 7:
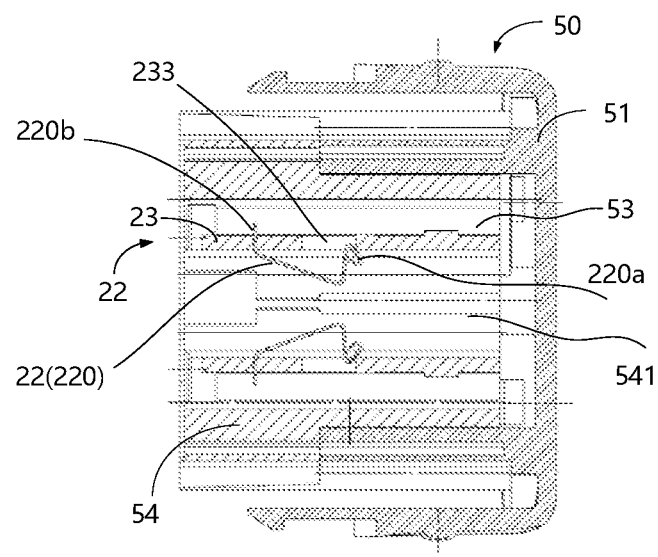
FIG. 7 is a sectional view of the battery pack of an embodiment of the application.
Figure 11:
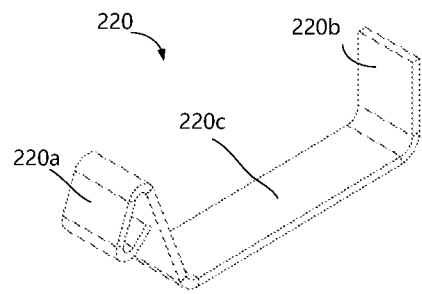
FIG. 11 is a schematic structural view of an elastic piece of an embodiment of the application.

As shown in FIG. 7 specifically, in the present embodiment, the discharging circuit board 23 is disposed on a side wall of the recess 541 of the frame 54 of the battery pack 50. It should be understood that the discharging circuit board 23 may also be arranged on other places of the battery pack 50 for convenient operation. The switching member 22 is specifically configured as a movable member that is conductive, at least part of the movable member may be operated to move, and at least part of the movable member may be an elastic part, and specifically may be an elastic piece 220, as shown in FIG. 6 and FIG. 7, an aperture 233 is disposed in the discharging circuit board 23, and at least part of the elastic piece 220 is disposed in the aperture 233. Furthermore, the elastic piece 220 comprises a fixed portion 220b which is fixed in the discharging circuit board 23 and in electrical connection with the discharge element 21; a movable portion 220a operably to be connected to the discharging circuit board 23, and operably to be electrically connected to the discharge element 21; and a transition portion 220c which formed between the fixed portion 220b and the movable portion 220a (as shown in FIG. 11). The movable portion 220a of the elastic piece 220 may be operated to change the position thereof, such that the switching member 22 may be operated to switch between the initial open state, the intermediate open state, and the closed state.

Specifically, when the battery pack 50 is in the initial unused state, the switching member 22 is positioned in the initial open state, i.e. the movable portion 220a of the elastic piece 220 bias against the proximal wall of the aperture 233 of the discharging circuit board 23, as shown in FIG. 7, where the movable portion 220a of the elastic piece 220 is not in electrical communication with the discharge element 21, the discharge circuit is not conducting, which forms the first state of the discharging system 20.

Figure 8:
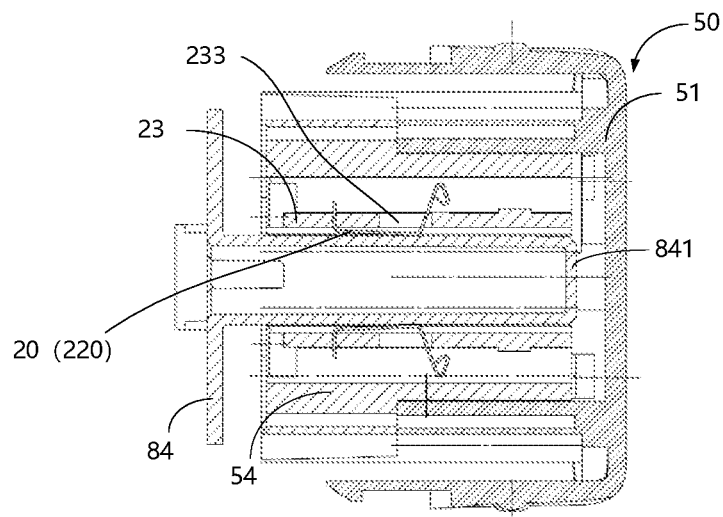
FIG. 8 is a sectional view of the battery pack of an embodiment of the application, in which the protruding portion is in contact with the switching member.

When the battery pack 50 is assembled in the battery dock 88 of the surgical instrument 100, the protruding portion 841 is inserted into the recess 541 along an extending direction of the recess 541, and the switching member 22 is operated to be switched to the intermediate open state, i.e., a transition portion 220c of the elastic piece 220 is actuated by the protruding portion 841 so as to drive the movable portion 220a to pass through the aperture 233 along the proximal wall thereof, and the movable portion 220a is biased by the protruding portion 841 so as to be disconnected with the discharging circuit board 23, such that the switching member 22 is maintained to be positioned in the intermediate open state, and where the discharge circuit is non-conductive, forming the second state of the discharging system 20, as shown in FIG. 8. It should be understood that the aperture 233 provides space, allowing at least part of the switching member 22 to move, such that at least part of the switching member 22 may be operated to move therein, and to be pass through as well. Therefore, the aperture 233 may also be configured in other shapes, such as a groove, a special-shaped groove, a special-shaped hole, etc.

Figure 9:
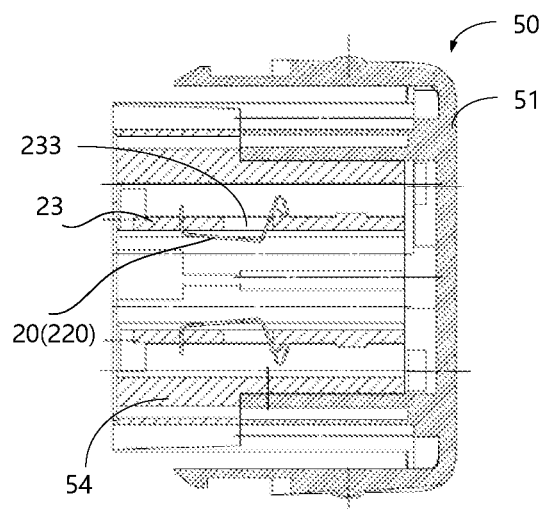
FIG. 9 is a sectional view of the battery pack of an embodiment of the application, in which the protruding portion is separated from the switching structure.

When the surgical instrument 100 completes the surgical operation, the battery pack 50 is removed from the surgical instrument 100, and the protruding portion 841 is removed from the recess 541 as well. Under elastic force provided by the transition portion 220c, the movable member 220a of the elastic piece 220 is moved towards the discharging circuit board 23 and contacted with the discharging circuit board 23, so as to be further electrically connected with the discharge element 21, such that, the switching member 22 is switched in the closed state, and the discharge circuit is conducting, forming the third state of the discharging system 20, as shown in FIG. 9. It should be understood that the protruding portion 841 may also be arranged on the base assembly 84 or the grip portion of the handle assembly 80.

Figure 12:
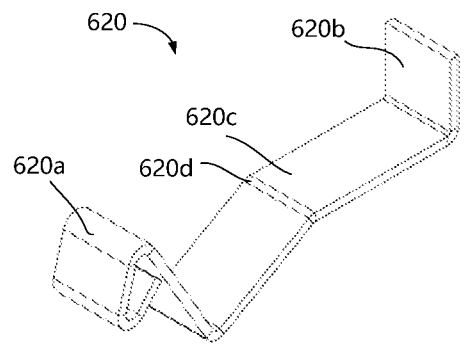
FIG. 12 is a schematic structural view an elastic piece of another embodiment of the application.

Furthermore, as shown in FIG. 11 and FIG. 12, a guide surface may be arranged on the movable portion 220a of the elastic piece 220. When the transition portion 220c is operated, the guide surface has a guiding effect for the smooth position transition of the movable portion 220a, which is convenient for the movable member 220a to enter the aperture 233 smoothly.

Figure 10:
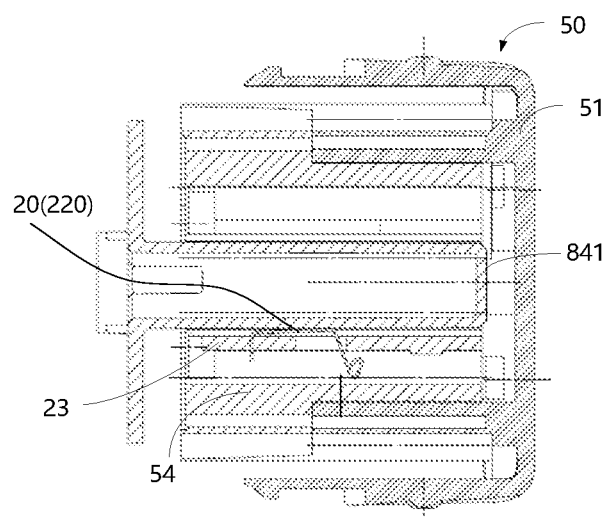
FIG. 10 is a schematic structural view of an embodiment of the application having one circuit board.

It should be understood that the battery pack 50 may comprise at least one discharging systems 20 described in one of the embodiments. For example, one discharging circuit board 23 may be arranged on the side wall of the recess 541, as shown in FIG. 10, or two discharge circuit boards 23 may be arranged on the side walls of the recess 541 in a symmetrical or asymmetric manner, as shown in FIGS. 7-9, other arrangement may be set, and specifically, the discharge circuit board may also be arranged on a proximal side of the recess 541. It should be understood that a discharge speed of the battery pack 20 may be increased for rapidly discharging by using a plurality of discharging systems 20 to discharge simultaneously.

Furthermore, FIG. 11 shows a specific structure of the elastic piece 220. The elastic piece 220 comprises a fixed portion 220b and a movable portion 220a, and a transition portion 220c arranged therebetween. A certain angle is formed by the fixed portion 220b and the transition portion 220c. For example, the fixed portion 220b may be arranged perpendicular to the transition portion 220c; the movable portion 220a and the transition portion 220c are also arranged with a certain angle, for example, an acute angle is formed between the movable portion 220a and the transition portion 220c, facilitating the elastic piece 220 to be moved to the corresponding position. Certainly, the movable portion 220a and the transition portion 220c of the elastic piece 220 may also be arranged in other manners for easy to be operated.

Alternatively, for example, as shown in FIG. 12, the transition portion 620c of the elastic piece 620 comprises a bent portion 620d. Such arrangement of the bent portion 620c weakens the rigidity of the transition portion 620c, which makes it easier for the elastic piece 620 to be operated to move, such that bias force applied during operation is reduced. It should be understood that the transition portion of the elastic piece in this embodiment may also be designed into other structures with weakening effect.

Embodiment 2

FIGS. 13 to 19 show the specific structures of the surgical instrument 100, the battery pack 50 and the discharging system 20 in an alternative embodiment of the present disclosure, in which the switching member 22 of the discharging system 20 is arranged at a proximal side of the recess 541 of the frame of the battery pack 50, or the switching member 22 may also be arranged in other ways, for example, it may also be arranged on the side wall of the recess 541 to be electrically connected to the discharge element 21, and the discharging circuit board 23 may be arranged between the frame 54 and the housing 51.

Figure 13:
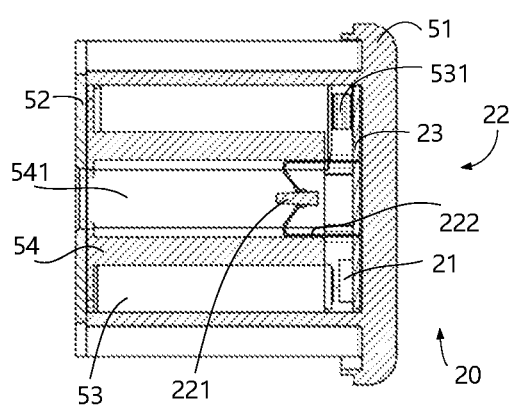
FIG. 13 is a sectional view of a battery pack of another embodiment of the application.

Referring to FIG. 13, in this embodiment, the switching member 22 of the discharging system 20 comprises a blocking member 221 and a conductive member. The conductive member comprises at least two separable conductive elastic members, i.e. conductive elastic pieces 222. One end of each conductive elastic piece 222 is a fixed end fixed on the discharging circuit board 23 and electrically connected to the discharge element 21. The other end of each the conductive elastic piece 222 is a free end. The blocking member 221 is arranged between the free ends of at least two conductive elastic pieces 222 to operably separate the conductive elastic pieces 222 from each other, preventing the conductive member being electrical conducting. It should be understood that the function of the blocking member described in one of the embodiments of the present disclosure is to make the switching structure 22 being positioned in the initial open state, where, the discharge circuit is non-conductive, and the blocking member may be operated to be functionally disabled for blocking and the switching member is switched into the intermediate open state.

The term "blocking" may be either a physical blocking or an electrical blocking, as long as it may keep the switching member in the initial open state.

Specifically, as shown in FIG. 13, when the battery pack 50 is in the initial unused state, the blocking member 221 of the discharging system 20 is biasing free ends of the conductive elastic pieces 222 to be separated from each other, preventing the conductive member from being electrical conducting, and the switching member 22 is positioned in the initial open state, while the discharging system 20 is in the first state.

Figure 14:
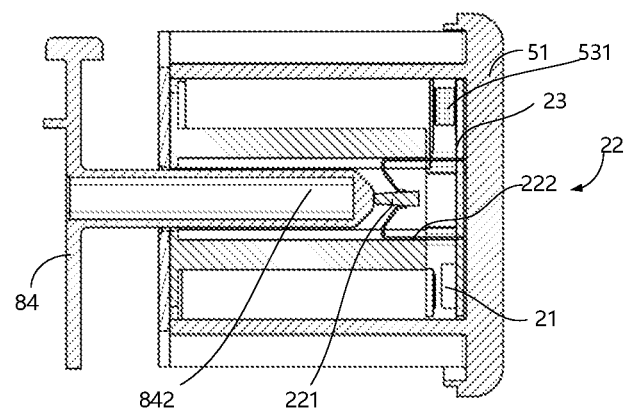
FIG. 14 is a sectional view of the battery pack of another embodiment of the application, in which the protruding portion abuts against the blocking member.
Figure 15:
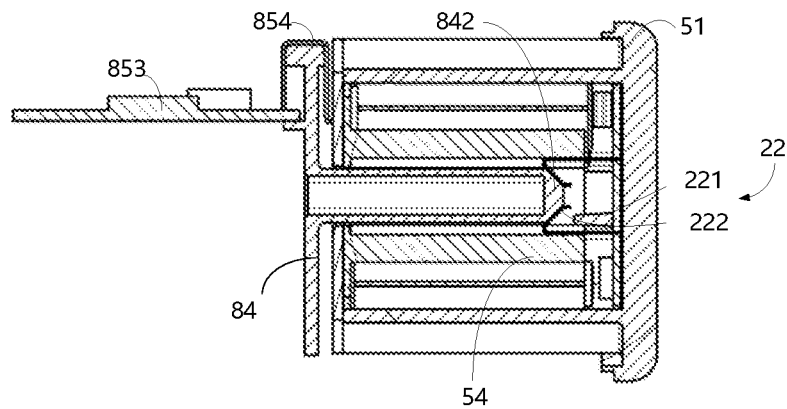
FIG. 15 is a sectional view of the battery pack in another embodiment of the application, in which the protruding portion pushes the blocking member until to fall.

As shown in FIG. 14, when the battery pack 50 is assembled in the battery dock 88 of the surgical instrument 100, the protruding portion 842 is inserted into the recess 541 along an extending direction of the recess 541, and abuts against the blocking member 221. The blocking member 221 is actuated by the proximal end of the protruding portion 842 and released from the conductive elastic piece 222. As shown in FIG. 15, the conductive elastic pieces 222 are remained to be isolated from each other through the proximal end of the protruding portion 842, preventing the conductive member to be electrical conductive, where the switching member 22 is remained in the open state, i.e., the intermediate open state, and the discharging system 20 is in the second state.

Figure 16:
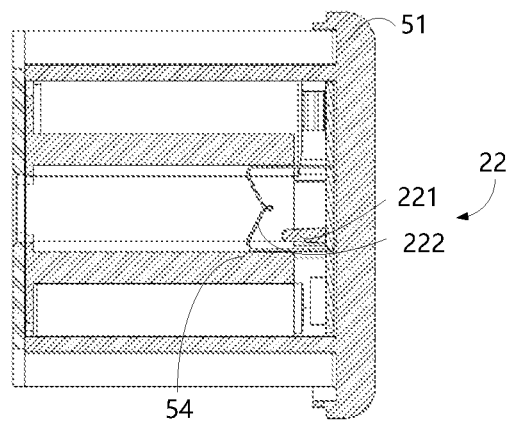
FIG. 16 is a schematic structural view the battery pack of another embodiment of the application, in which free ends of the conductive elastic strip are in contact with each other.

When the surgical instrument 100 completes the surgical operation, the battery pack 50 is removed from the surgical instrument 100, and the protruding portion 842 is removed from the recess 541 as well as the conductive elastic pieces 222 of the conductive member, where, as shown in FIG. 16, the conductive elastic pieces 222 contact with each other so as to be conductive, the switching member 22 is switched to the closed state, and the discharging system 20 comes to the third state, the discharging element 21 and the battery unit 53 are conducting, and the battery unit 53 starts to be discharged. The protruding portion 842 may be arranged on the base assembly 84 or the grip part of the handle assembly.

Figure 17:
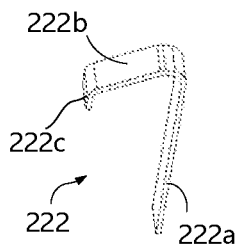
FIG. 17 is a schematic structural view of a conductive member of another embodiment of the application.

FIG. 17 shows the specific structure of the conductive elastic piece 222 which comprises an elastic body 222a having a first end (i.e. a fixed end) connected to the discharging circuit board 23, and a second end having a bended portion 222b which extends toward the other conductive elastic piece 222 arranged on the opposite side thereof, inclining towards the first end in the extending direction, so as to be convenient for locating the blocking member 221. The blocking member 221 is arranged between the two bended portions 222b when the discharging system 20 is in the first state. In addition, the conductive elastic piece 222 also comprises a fitting portion 222c disposed on the bended portion 222b. The fitting portion 222c is arranged such that a line contact formed by the two oppositely disposed bended portions locating the blocking member 221 turns to a face contact, which leads to an increased contact area between the conductive elastic piece 222 and the blocking member 221, providing more stable location, so as to prevent the blocking member 221 from falling during transportation.

Figure 18:
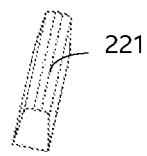
FIG. 18 is a schematic view of a blocking member of another embodiment of the application.

FIG. 18 shows the specific structure of the blocking member 221. The blocking member 221 has a columnar structure and has a slope surface inclined towards a center line of the columnar structure; the blocking member 221 is configured to have this shape, such that when the blocking member 221 is located between two conductive elastic pieces 222, it is convenient for the amounting of the blocking member 221; where, it also facilitates the protruding portion 842 to push the blocking member 221 to be released from arrangement between the two conductive elastic pieces 222. Since the blocking member 221 is adapted for to isolate the conductive elastic pieces 222, the blocking member 221 is configured as an insulating member.

Embodiment 3

Figure 20:
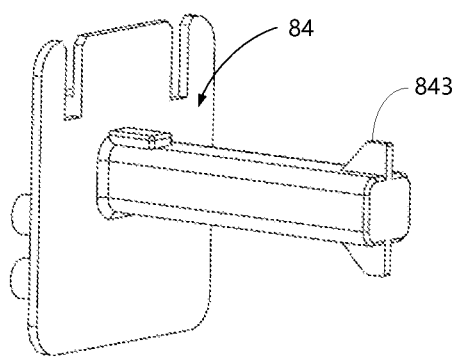
FIG. 20 is a schematic structural view a protruding portion of another embodiment of the application.
Figure 21:
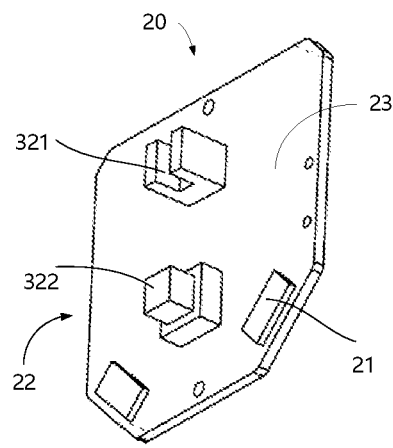
FIG. 21 is a schematic structural view of a discharging circuit board of a further embodiment of the application.

FIGS. 20 to 24 show an alternative embodiment of the battery pack 50 and the discharging system 20 of the present disclosure. Alternatively, as shown in FIG. 21, on the basis of the abovementioned embodiments, the switching member 22 of the discharging system 20 comprises a blocking member and a conductive member, and the blocking member is specifically configured as a first switch 321, the conductive member is specifically configured as a second switch 322 and the first switch 321 and the second switch 322 are both arranged on the discharging circuit board 23.

Furthermore, as shown in FIG. 20, a protruding portion is arranged on the base assembly 84, provided with a fin portion 843 which is adapted to operably cooperate with the first switch 321 and/or the second switch 322. The protruding portion may be arranged on the base assembly 84 or the grip part of the handle assembly.

Figure 22:
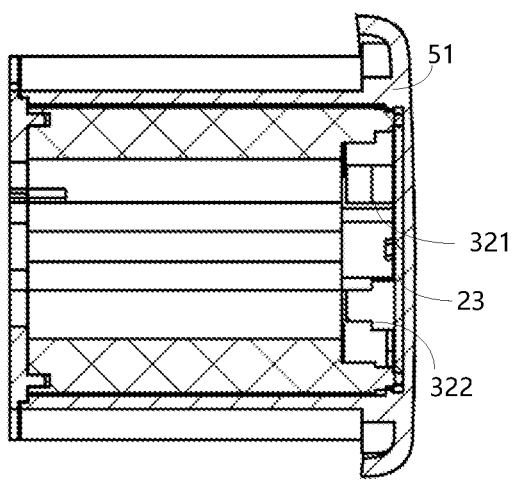
FIG. 22 is a sectional view of a battery pack of a further embodiment of the application.
Figure 23:
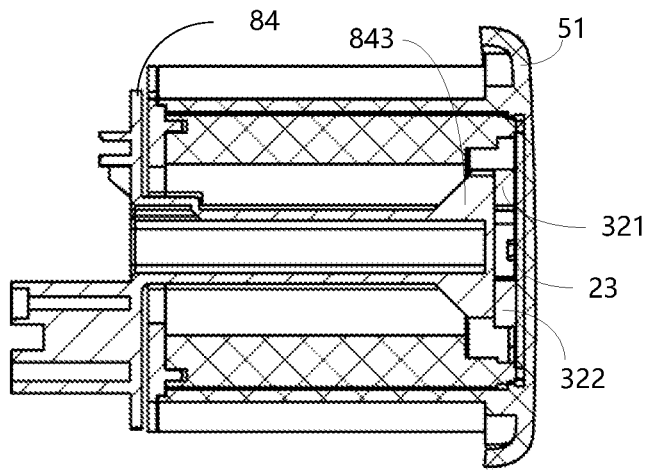
FIG. 23 is a sectional view of the battery pack of another embodiment of the application, in which a protruding portion abuts against a blocking member.
Figure 24:
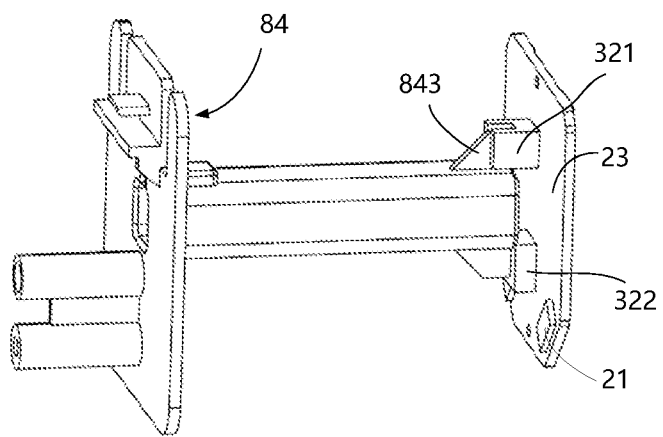
FIG. 24 is a schematic structural view of a further embodiment of the application, in which a protruding portion abuts against a blocking member.

Specifically, as shown in FIG. 22, when the battery pack 50 is in the initial unused state, the first switch 321 remains switched off, and the second switch 322 is not conducting, where the switching member 22 is in the initial open state, and the discharging system 20 is in the first state.

When the battery pack 50 is assembled in the battery dock 88 of the surgical instrument 100, the protruding portion and the fin portion 843 are inserted into the recess 541 along an extending direction of the recess 541. The fin portion 843 interacts with the first switch 321 such that the switch 321 is conducting, while the second switch remains in the turn-off state due to the engagement of the fin portion 843, i.e., the conductive member remains in a non-conductive state, where the switching member 22 is in the intermediate open state, and the discharging system 20 is in the second state.

When the surgical instrument 100 completes the surgical operation, the battery pack 50 is removed from the surgical instrument 100, and the protruding portion and the fin portion 843 are operated to be removed out of the recess 541 as well, where the second switch 322 is switched to be conductive without the engagement with the fin portion 843, such that the switching member 22 is switched to the closed state, and the discharging system 20 is switched to the third state, where the discharging element 21 and the battery unit 53 are conducting, and the battery unit 53 starts to be discharged.

Preferably, the first switch 321 described in this embodiment is a self-locking switch, allowing the first switch remains in the previous state, i.e., a conducting state, after being disengaged with the fin portion 843. In addition, the second switch 322 described in this embodiment is preferably an electronic switch, such as a photoelectric switch, which is composed of a light emitting end and a light receiving end. When the discharging system 20 is in the second state, the photoelectric switch remains in a non-conductive state due to the blocking of the fin portion 843. As the fin portion 843 is removed from the recess 541, the photoelectric switch is no longer blocked, and a connection may be established between the transmitting end and the receiving end, so that the photoelectric switch is conducting, and the discharging system 20 is switched to the third state, thereby self-discharge function of the battery unit 53 of the battery pack 50 is realized.

More specifically, the arrangement of the fin portion 843 may be set according to the positions of the first switch 321 and the second switch 322. In addition, the first switch 321 and the second switch 322 may also be selected from other suitable switching elements, as long as they may comply with the above functional principles.

Embodiment 4

Figure 25:
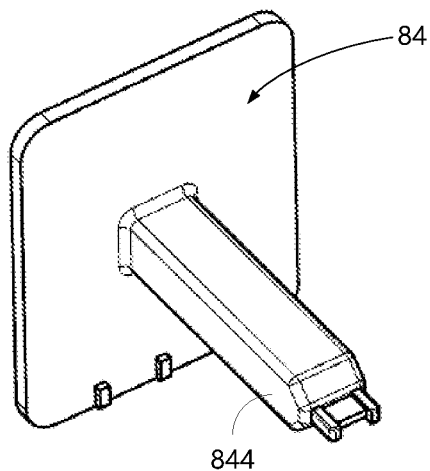
FIG. 25 is a schematic structural view of a protruding portion of a further embodiment of the application.
Figure 26:
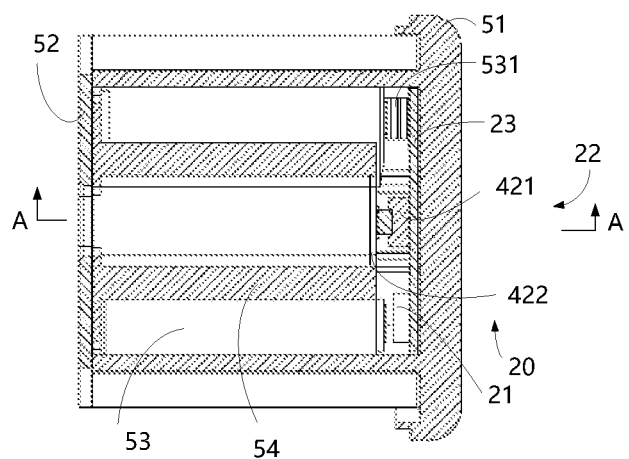
FIG. 26 is a sectional view of a battery pack of a further embodiment of the application.
Figure 27:
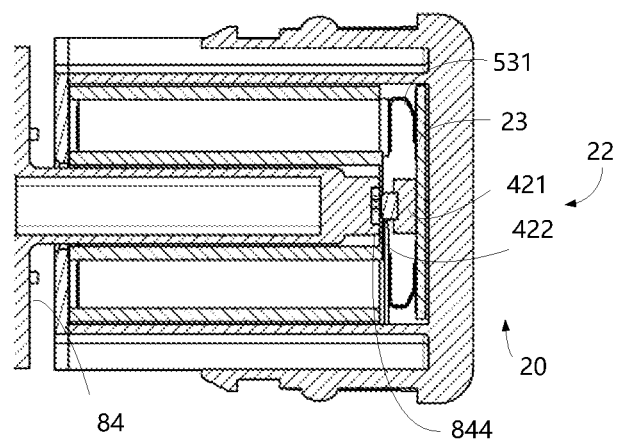
FIG. 27 is a sectional view of a battery pack in a direction of A-A in FIG. 26, illustrating a protruding portion abuts against the blocking member.
Figure 28:
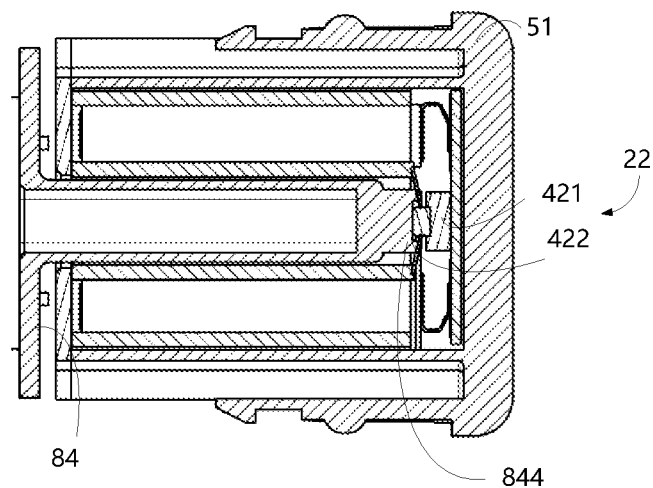
FIG. 28 is a sectional view in a direction of A-A in FIG. 26, illustrating a protruding portion abutting against a stop member until breaking.
Figure 29:
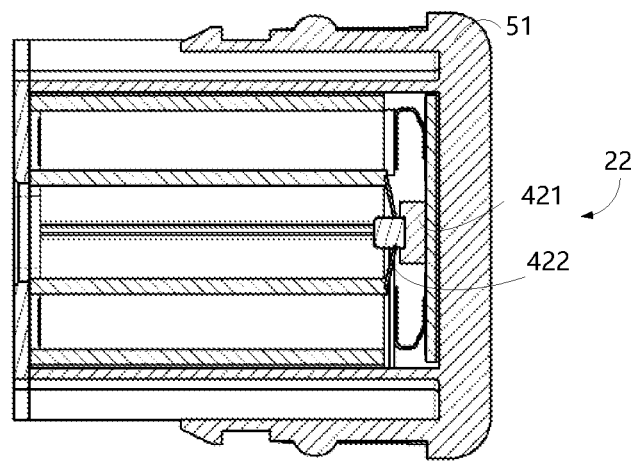
FIG. 29 is a schematic structural view in a direction of A-A in FIG. 26, illustrating a battery pack is used.

FIGS. 25 to 29 show still another embodiment of the battery pack 50 and its discharging system 20 described in the present disclosure. As an alternative embodiment, on the basis of the abovementioned embodiments, the conductive member of the switching member 22 of the discharging system 20 is configured as a normal-close switch 421, and the blocking member is a stop member. For example, in this embodiment, the stop member is configured as a limit plate 422, and the limit plate 422 is configured to abut against the normal-close switch 421, such that the switch 421 is in initial switched-off (open) state, as shown in FIG. 26.

As further shown in FIG. 25, a tip is arranged on a proximal end of the protruding portion 844 of this embodiment, which is adapted to operably break the limit plate 422, such that the limit plate 422 capable of maintaining the normal-close switch 421 in the switched-off state without blocking. The stop member 422 may be made of a brittle sheet material that is easy to be broken by operation, or the stop member 422 may be provided with indentations to facilitate the breaking by operation thereof.

Specifically, as shown in FIG. 26, when the battery pack 50 is in the initial unused state, the limit plate 422 abuts against the normal-close switch 421, forcing it in the switched-off state, where, the switching member 22 is in the initial open state, and the discharging system 20 is in the first state.

When the battery pack 50 is assembled in the battery dock 88 of the surgical instrument 100, the protruding portion 844 and the tip are inserted into the recess 541 along the extending direction of the recess 541, and the tip is in contact with the stop member 422 and causes it to break. At this time, the normal-close switch 421 is remained in the switched off state due to engagement with the protruding portion 844, i.e., the conductive member remains in the non-conductive state, where, the switching member 22 is in the intermediate open state, and the discharging system 20 is in the second state.

When the surgical instrument 100 completes surgical operation, the battery pack 50 is removed from the surgical instrument 100, and the protruding portion 844 and the tip are removed from the recess 541 as well, where the normal-close switch 421 is conducting due to being disengaged with the limit plate 422, and the switching member 22 is switched to the closed state, the discharging system 20 is switched to the third state, where the discharging element 21, the battery unit 53 are conducting, and the battery unit 53 starts to be discharged.

It should be understood that the normal-close switch described in this embodiment refers to a switch in the closed state without external force. When a switch button is toggled or the switch is controlled by an automatic device to toggle, the switch is switched to an open circuit. For example, the normal-close switch may be a travel switch, a pressure relay, etc.

More specifically, the arrangement of the tip of the protruding portion 844 may be made according to the shape of the normal-closed switch 421 on its own, and the protruding portion 844 may be arranged on the base assembly 84 or the grip part of the handle assembly. The position of the limit plate 422 may also be set according to the switched off position of the normal-close switch 421, as long as it may meet the above functional principle.

The above embodiments are merely for clear description, and are not intended to limit the detailed description of the embodiments. For a person skilled in the art, other changes or modifications in different forms may be made on the basis of the above description. It is not necessary and impossible to list all the embodiments here. The obvious changes or modifications derived therefrom still fall within the scope of the present disclosure.

What is claimed is:

1. A surgical instrument, comprising:
   a handle assembly, having a protruding portion; and
   a battery pack, detachably assembled on the handle assembly, and operatively coupled to the protruding portion, and having at least one battery unit; wherein, the battery pack comprises at least one discharging system comprising:
   a discharge element, and
   a switching member, operable to electrically connect the discharge element to the battery unit of the battery pack to form a discharge circuit; wherein,
   the switching member has an initial open state, in which the discharge circuit is non-conductive; an intermediate open state, in which the switching member cooperates with the protruding portion to make the discharge circuit non-conductive, and a closed state, in which the switching member is released from the protruding portion to make the discharge circuit conducting;
   wherein the discharging system further comprises a discharging circuit board, on which the discharge element is arranged, and the switching member is configured to be at least one conductive movable member with at least part operably movable, and
   one end of the movable member is fixed on the discharging circuit board and electrically connected to the discharge element, and the other end thereof is operably connected to the discharge element electrically.

2. The surgical instrument according to claim 1, wherein when the switching member is in the intermediate open state, the protruding portion forces the movable member at a position where the movable member is in non-conductive connection with the discharge element.

3. The surgical instrument according to claim 2, wherein the movable member comprises a fixed portion, a movable portion, operably to be electrically connected to the discharge element, and a transition portion, arranged between the fixed portion and the movable portion.

4. The surgical instrument according to claim 3, wherein when the switching member is in the initial open state, the movable portion of the movable member abuts against a side wall of an aperture arranged on the discharge circuit board, and is non-conductively connected to the discharge element.

5. The surgical instrument according to claim 1, wherein the switching member comprises a blocking member and a conductive member, and
   the blocking member and/or the conductive member are/is operable to switch the switching member between the initial open state, the intermediate open state and the closed state.

6. The surgical instrument according to claim 5, wherein the blocking member is adapted for causing the switching member to be in the initial open state, and is operated by the protruding portion to be disabled from blocking the switch member, so as to cause the switching member to be in the intermediate open state; wherein the switching member is arranged on a proximal side of the recess of a frame of the battery pack, and is electrically connected to the discharge element.

7. The surgical instrument according to claim 5, wherein the conductive member comprises separable conductive elastic pieces, wherein when the switching member is in the initial open state, the blocking member is arranged between free ends of the conductive elastic pieces to isolate the conductive elastic pieces from each other.

8. The surgical instrument according to claim 5, wherein the blocking member is actuated by the protruding portion to be released from the conductive member.

9. The surgical instrument according to claim 5, wherein when the switching member is in the intermediate open state, the protruding portion is respectively in contact with the free ends of the conductive elastic pieces, so as to isolate the conductive elastic pieces from each other.

10. The surgical instrument according to claim 5, wherein when free ends of the conductive elastic members are engaged with each other, the switching member is switched to the closed state, and the discharge circuit is conducting.

11. The surgical instrument according to claim 5, wherein the blocking member is configured as a first switch, and the conductive member is configured as a second switch; wherein the first switch is operable to control the second switch.

12. The surgical instrument according to claim 5, wherein the blocking member is configured as a stop member, and the conductive member is configured as a normal-close switch.

13. The surgical instrument according to claim 1, wherein the switching member comprises a blocking member, and a conductive member having a separable conductive elastic piece, wherein when the switching member is in the initial open state, the blocking member is arranged between free ends of the conductive elastic pieces to isolate the conductive elastic pieces from each other.

14. The surgical instrument according to claim 1, wherein the switching member comprises a first switch and a second switch, and the first switch and/or the second switch are/is operable to be electrically connected with the discharge element, so as to switch the switching member between the initial open state, the intermediate open state and the closed state.

15. The surgical instrument according to claim 1, wherein the switching member comprises a normal-close switch, the state of which is depended on a stop member, wherein the stop member is operated to switch the switching member between the initial open state, the intermediate open state, and the closed state.

16. A battery pack comprising at least one battery unit, further comprising at least one discharging system having:
a discharging element, and
a switching member, operably to be in electrical connection with the discharging element to the battery unit of the battery pack to form a discharge circuit;
the switching member has an initial open state, in which the discharge circuit is non-conductive, an intermediate open state, in which the switching member is operated to cause the discharge circuit to be non-conductive, and a closed state, in which the switching member is operated to allow the discharge circuit to be conductive;
wherein the discharging system further comprises a discharging circuit board provided with the discharging element, and the switching member is configured to be at least one conductive movable member, and at least portion of the conductive movable member is operated to move, and one end of the conductive movable member is fixed on the discharging circuit board and electrically connected to the discharge element, and the other end of the conductive movable member is operated to be electrically connected to the discharge element.

17. The battery pack according to claim 16, wherein the switching member comprises a blocking member and a conductive member, and the blocking member and/or the conductive member are/is operable to switch the switching member between the initial open state, the intermediate open state and the closed state.

18. The battery pack according to claim 16, wherein the switching member comprises a blocking member, and a conductive member that comprises a separable conductive elastic piece, and when the switching member is in the initial open state, the blocking member is arranged between free ends of the conductive elastic pieces to isolate the conductive elastic pieces from each other.

* * * * *